United States Patent [19]

Schlossman et al.

[11] Patent Number: 5,935,801
[45] Date of Patent: Aug. 10, 1999

[54] MONOCLONAL ANTIBODY THAT DETECTS APOPTOTIC ANTIGEN

[75] Inventors: Stuart Franklin Schlossman, Newton Centre; Chonghui Zhang, Brookline, both of Mass.

[73] Assignee: Dana-Farber Cancer Institute, Boston, Mass.

[21] Appl. No.: 08/623,876

[22] Filed: Mar. 29, 1996

[51] Int. Cl.$^6$ .................................................. G01N 33/53
[52] U.S. Cl. ......................... 435/7.91; 435/7.9; 435/29; 435/332; 435/336; 435/346; 530/388.2; 530/388.7; 436/538
[58] Field of Search .............................. 530/388.2, 387.1, 530/388.7; 435/29, 7.9, 7.91, 240, 26, 240.27, 332, 336, 346; 436/538

[56] References Cited

FOREIGN PATENT DOCUMENTS

| 0510691A1 | 10/1992 | European Pat. Off. . |
| 0511202B1 | 6/1994 | European Pat. Off. . |
| 6109729 | 4/1994 | Japan . |
| 9077794 | 3/1997 | Japan . |
| WO92/17193 | 10/1992 | WIPO . |
| WO 00642 | 1/1995 | WIPO . |

OTHER PUBLICATIONS

Journal of Immunology, vol. 157, Nov. 1996, pp. 3980–3987, Zhang et al., "A mitochondrial membrane protein defined by a novel monoclonal antibody is preferentially detected in apoptotic cells.".

Ajmani,A.K.,M.Satoh,E.Reap, P.L. Cohen, and W.H. Reeves.1995.Absence of autoantigen Ku in mature human neutrophils and human promyelocytic leukemia line (HL–60) cell and lymphocytes undergoing apoptosis.J.Exp. Med. 181:2049–2058.

Anderson,P.,M.–L.Blue,C.O'Brien, and S.F.Schlossman.1989. Monoclonal antibodies reactive with the T cell receptor chain: production and characterization using a new method.J.Immunol.143 1899–1904.

Barry,M.A., and A. Eastman.1993. Identification of deoxyribonuclease II as an endonuclease involved in apoptosis. Arch. Biochem.Biophys. 300:440–450.

Boehmer,H.von.1992.Thymic selection: a matter of life and death. Immunology Today 13:454–458.

Clarke,P.G.H.1990.Developmental cell death: morphological diversity and multiple mechanisms. Anal.Embryol. 181:195–213.

Casciola–Rosen,L.A.,G.Anhalf,and A.Rosen. 1994.Autoantigens targeted in systemic lupus erythematosus are clustered in two populations of surface structures on apoptotic keratinocytes.J.Exp.Med. 179:1317–1330.

Cobbold,S.P.,and H.Waldmann.1981. A rapid solid–phase enzyme–linked binding assay for screening monoclonal antibodies to cell surface antigens.J. Immunol. Meth.44:125–133.

Duke,R.C.,R. Chervenak, and J.J. Cohen. 1983. Endogenous endonuclease–induced DNA fragmentation: an early event in cell–mediated cytolysis. Proc. Natl. Acad.Sci. USA 80:6361–6365.

Estus,S.,W.J.Zaks,R.S. Freeman, M. Gruda, R. Bravo, and E.M.Johnson Jr. 1994. Altered gene expression in neurons during programmed cell death:Identification of c–Jun, as necessary for neuronal apoptosis.J.Cell Biol. 127:1717–1727.

Fernendez,P.A.,R.J.Rotello,Z. Rangini, A.Doupe,H.C.A. Drexler, and J. Yuan. 1994 Expression of a specific marker of avian programmed cell death in both apoptosis and necrosis. Proc. Natl. Adac.Sci.USA 91:8641–8645.

Fiskum,G.,S.W.Craig,G.L. Decker,and A.L.Lehninger. 1980. The cytoskeleton of digitonin–treated rat hepatocytes. Pros. Natl. Acad.Sci. USA 77:3430–3434.

Gougeon M.–L.,and L.Montagnier.1993. Apoptosis in AIDS.Science 260:1269–1270.

Griffiths,G., and H.Hoppeler.1986. Quantitation in immunocytochemistry: correlation of immunogold labeling to absolute number of membrane antigens.J.Histochem. Cytochem.34:1389–1398.

Hennet,T.G. Bertoni, C.Richter, and E.Peterhens. 1993a. Expression of Bcl–2 protein enhances the survival of mouse fibrosarcoid cells in tumor necrosis factor–mediated cytotoxicity. Cancer Res. 53:1456–1460.

Hennet,T.C.Richter, and E. Peterhans.1993b. Tumor necrosis factor–α induced superoxide anion generation in mitochondria of L929 cells. Biochem.J. 289:587–592.

Hockenbery,T.,G.Nuñez,C.Milliman,R.D. Schreiber,and S.J.Korsmeyer. 1990.Bcl–2 is an inner mitochondrial membrane protein that blocks programmed cell death. Nature 248:334–346.

Itoh,N.S. Yonehara,A.Ishii,M.Yonehara,S. Mizushima, M.Sameshima, A.Hase, Y.Seto, and S. Nagata. 1991. The polypepide encoded by the cDNA for human cell surface antigen Fas can mediate apoptosis. Cell 66: 233:243.

Jacobson,M.D.,J.F.Burne, M.P.King,T. Miyashista, J.C.Reed, and M.C.Raff. 1993. Bcl–2 blocks apoptosis in cells lacking mitochondrial DNA. Nature 361:365–369.

(List continued on next page.)

*Primary Examiner*—Christina Y. Chan
*Assistant Examiner*—Patrick J. Nolan
*Attorney, Agent, or Firm*—Mitchell E. Alter

[57] ABSTRACT

A monoclonal antibody which specifically binds to an antigen on the membrane of mitochondria in apoptotic cells. The antigen is a 38 kD protein that is detectable in cells undergoing apoptosis and undetectable in normal cells. This selectivity of the monoclonal antibody provides a method of distinguishing between normal and apoptotic cells in a sample of human hemopoietic cell populations. A method for detecting and measuring cells undergoing apoptosis is also provided.

8 Claims, 11 Drawing Sheets

OTHER PUBLICATIONS

Kearney,J.F.,A.Radbruch,B.Liesegang, and K.Rajewsky 1979. A new mouse myeloma cell line that has lost immunoglobulin expression but permits the construction of antibody–secreting hybrid cell lines. J.Immunol.123:1548–1550.

Kerr,J.F.R.,A.H.Wyllie,and A.R.Currie.1972. Apoptosis: a basic biological phenomenon with wide–ranging implication in tissue kinetics. Br.J.Cancer 26:239–257.

Kishimoto,H.,C.D. Surn,and J.Sprent.1995.Upregulation of surface markers on dying thymocytes. J.Exp.Med. 181:649–655.

Koopman,G.,C.P.M.Reutelingsperger, G.A.M. Kuijten, R.M.J.Keehnen,S.T. Pals, and M.H.J. van Oers.1994. Annexin V for flow cytometric detection of phosphatidylserine expression on B cells undergoing apoptosis. Blood 184:1415–1420.

Köhler,G.,and C.Milstein.,1975.Continuous cultures of fused cells secreting antibody of predefined specificity. Nature 256:495–497.

Krajewski,S.,S. Tanaka,S.Takayama,M.J. Schibler, W.Fenton,and J.C.Reed. 1993.Investigation of the subcellular distribution of the bcl–2 oncoprotein: residence in the nuclear envelope, endoplasmic reticulum, and outer mitochondrial membranes. Cancer Res. 53:4701–4714.

Martin,S.J.1993. Protein or RNA synthesis inhibition induces apoptosis of mature human CD4+ T Cell blasts. Immunol. lett. 35:125–134.

Murgia,M.,P.Pizzo,D.Sandona, P.Zanovello, R. Rizzuto, and F. di Virgilio.1992. Mitochondrial DNA is not fragmented during apoptosis.J.Biol. Chem.267:10939–10941.

Nuñez,G.,L. London,D.Hockenbery, M.Alexander,J.P.McKearn,and S.J. Korsmeyer.1990. Deregulated Bcl–2 gene expression selectively prolongs survival of growth factor–deprived hemopoietic cell lines.J.Immunol.144:3602–3610.

Oehm,A.,I.Behrmann,W.Falk,M.Pawlita, G.Maier,C.Klas, M.Li–Weber,S. Richards,J. Dhein,B.C. Trauth,H.Postingl, and P.H. Krammer.1992. Purification and molecular cloning of the Apo–1 cell surface antigen, a member of the tumor necrosis factor/nerve growth factor receptor superfamily:Sequence identify with the Fas antigen.J.Biol.Chem.267–10709–10715.

Peitsch,M.C.,B.Polzar,H.Stephan,T.Crompton,H.R.MacDonald,H.G. Mannherz, and J.Tschop.1993. Characterization of the endogenous deoxyribonuclease involved in nuclear DNA degradation during apoptosis (programmed cell death). EMBO J. 12:371–377.

Robertson,M.J.,T.J.Manley,G.Pichert,C.Cameron,K.J.Cochran,H.Levine and J.Ritz.1995. Functional consequences of Apo–1/Fas (CD 95) antigen expression by normal and neoplastic hematopoietic cells.Leuk.Lymphoma 17:51–58.

Rotello,R.J.,P.A. Fernandez, and J.Yuan.1994. Anti–apogens and anti–engulfens: monoclonal antibodies reveal specific antigens on apoptotic and engulfment cells during chicken embryonic development. Development 120:1421–1431.

Smets,L.A.,J.van den Berg,D.Acton, B. Top,H. van Rooij, and M. Verwijs–Janssen.1994. BCL–2 expression and mitochondrial activity in leukemic cells with different sensitivity to glucocorticoid–induced apoptosis. Blood 5:1613–1619.

Steller,H., 1995. Mechanisms and genes of cellular suicide. Science 267:1445–1449.

Storrie,B., and E.A. Madden.1990. Isolation of subcellular organelles. In Methods in Enzymology.vol.182. Guide to protein purification. M.P. Deutscher, Editor, Academic Press, Inc., San Diego, CA 203–225.

Tepper,C.G., and G.P. Studzinki.1992. Teniposide induces nuclear but not mitochondrial DNA degradation. Cancer Res. 52:3384–3390.

Thompson,C.B. 1995.Apoptosis in the pathogenesis and treatment of disease. Science 267:1456–1462.

Trauth,B.C.,A.M.J.Klas S. Peters,P.M. Matzku,P.Möller, W.Falk,K.M. Debatin, and P.H.Krammer. 1989. Monoclonal antibody–mediated tumor regression by induction of apoptosis. Science 245:301–305.

Vaux,D.,S.Cory, and J.Adams.1988. Bcl–2 gene promotes haemopoietic cell survival and cooperates with c–myc to immortalize pre–B cells. Nature 335:440–442.

Vayssiere, J.L.,P.X.Petit, Y.Risler, and B. Mignotte.1994. Commitment to apoptosis is associated with changes in mitochondrial biogenesis and activity in cell lines conditionally immortalized with simian virus 40. Proc. Natl. Acad. Sci. USA 91:11752–11756.

Vukmanovic,S., and R. Zamoyska.1991. Anti–CD3–induced cell death in T cell hybridomas: mitochondrial failure and DNA fragmentation are distinct events. Eur.J.Immunol.21:419–424.

Wyllie,A.H.1980.Glucocorticoid–induced thymocyte apoptosis is associated with endogenous endonuclease activation.Nature 284:555–556.

Yoneda,M.,K.Katsumata,M.Hayakawa,M.Tanaka, and T. Ozawa.1995. Oxygen stress induces an apoptotic cell death associated with fragmentation of mitochondrial genome, Biochem. Biophys. Res. Comm. 209:723–729.

Zamzami,N.,P. Marchetti, M.Castedo, C. Zanin,J.L. Vayssiere, P.X. Petit, and G. Kroemer. 1995. Reduction in mitochondrial potential constitutes an early irreversible stop of programmed lymphocyte death in vivo.J.Exp.Med. 181:1661–1672.

Zhang C.H.,M.J. Robertson, and S.F. Schlossman.1995. A triplet of nuclease proteins ($NP^{42-50}$) is activated in human Jurkat cells undergoing apoptosis. Cell. Immunol. 165:161–167.

(x18,000 original magnification)

(x47,500 original magnification)

(x47,500 original magnification)

(C. x35,000; D, x72,500)

(C. x35,000; D, x72,500)

(x35,000 original magnification)

(x35,000 original magnification)

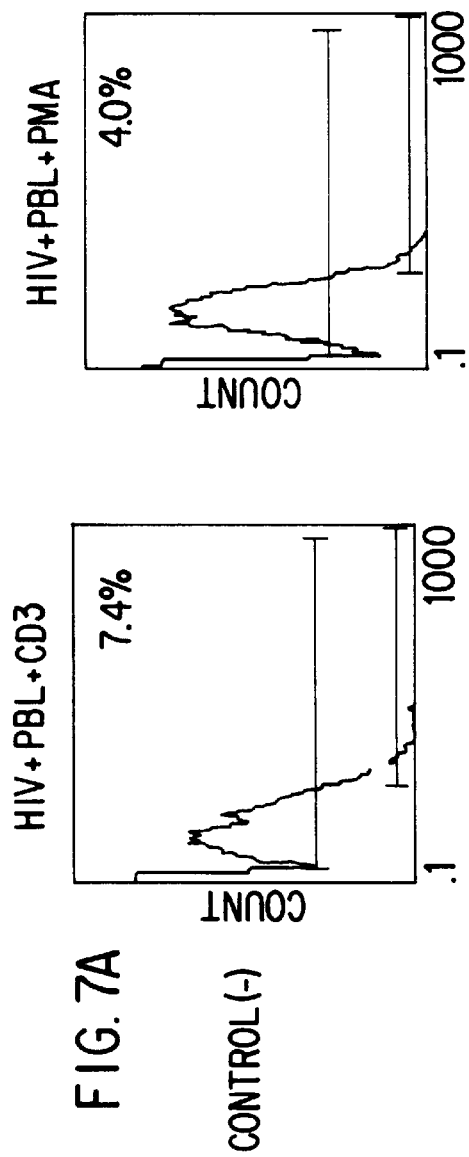
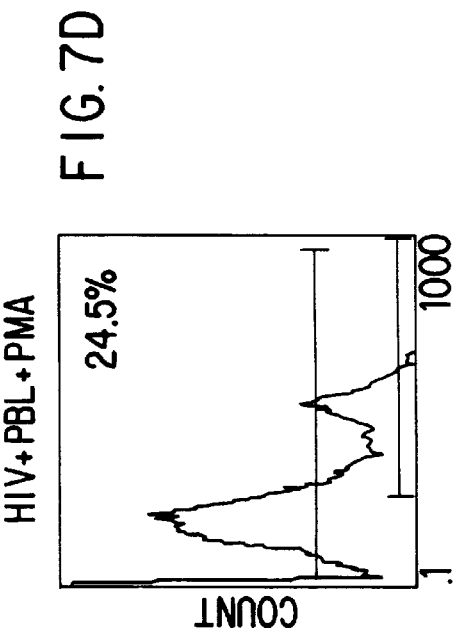
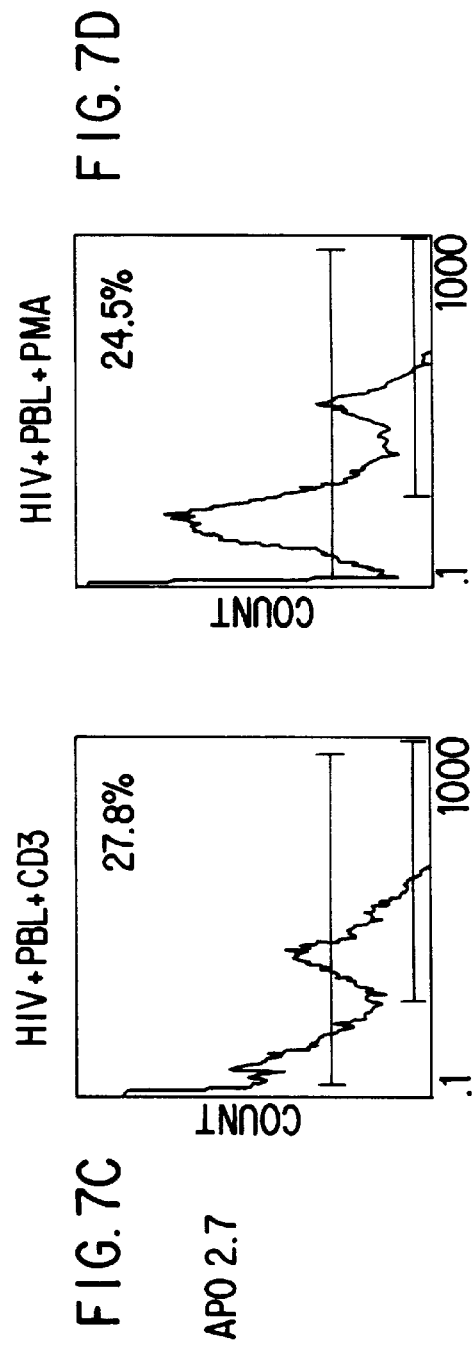
APO 2.7 STAINING OF PBL FROM HIV POSITIVE PATIENT
FIG. 7A CONTROL(-)
FIG. 7B
FIG. 7C APO 2.7
FIG. 7D

MONOCLONAL ANTIBODY THAT DETECTS APOPTOTIC ANTIGEN

FIELD OF THE INVENTION

This invention relates to monoclonal antibodies, and more particularly, relates to a monoclonal antibody which binds to a novel epitope on the mitochondrial membrane protein (7A6) which is exposed on cells undergoing apoptosis.

BACKGROUND OF THE INVENTION

Studies toward the biological and molecular understanding of programmed cell death have recently been stimulated by the identification of genes and their products which regulate apoptosis. Apoptosis represents an active process of autonomous cell death that occurs in physiological or pathological conditions (Clarke et al., 1990, Anal. Embryol. 181:195–213; Boehmer, 1992, Immunology Today 13:454–458; Gougeon and Matagnier et al., 1993, Science 260:1269–1270; Thompson, 1995, Science 267:1456–1462). Pathways to trigger programmed cell death may vary in different cells, but the regulation of apoptosis is generally mediated by the inducer and suppressor signals initiated from the molecular cascade during apoptosis. For instance, some members of the tumor necrosis factor/nerve growth factor receptor gene family are capable of inducing apoptotic cell death by perturbation of these molecules (Trauth et al., 1989, Science 245:301–305; Itoh et al., 1991, Cell 66:233–243; Oehm et al., 1992, J. Biol. Chem. 267:10709–10715), suggesting that they could act either by initiating a death-inducing signal or by blocking the signals required for cell survival. In contrast, the protein encoded by the Bcl-2 gene can promote cell survival by interfering with pathways leading to apoptosis although Bcl-2 does not appear to influence cell cycle progression (Vaux et al., 1988, Nature 335:440–442; Hockenbery et al., 1990, Nature 248:334–346; Nuñez et al., 1990, J. Immunol. 144:3602–3610). The recent identification of these genes and their products that regulate programmed cell death has contributed greatly to our understanding of the molecular mechanism of apoptosis, and also represents a new challenge in defining novel molecules involved in programmed cell death.

Apoptosis is accompanied by characteristic morphologic changes and the degradation of internucleosomal DNA (Kerr et al., 1972, Br. J. Cancer 26:239–257; Wyllie, 1980, Nature 284:555–556). Recent evidence indicates that, prior to the occurrence of morphological changes and death itself in the spontaneous or induced apoptosis, the cells undergo substantial alterations in both phenotypic and functional properties. These include activation of endonucleases (Duke et al., 1983, Proc. Natl. Acad. Sci. U.S.A. 80:6361–6365; Barry and Eastman, 1993, Arch. Biochem. Biphys. 300:440–450; Peitsch et al., 1993, EMBO J. 12:371–377; Zhang et al., 1995, Cell Immunol. 165:161–167), the expression of molecular markers (Estus et al., 1994, J. Cell. Biol. 127:1717–1727; Fernandez et al., 1994, Proc. Natl. Acad. Sci. U.S.A. 91:8641–8645), and a loss or increase in protein expression (Kishimoto et al., 1995, J. Exp. Med. 181:649–655; Casciola-Rosen et al., 1994, J. Exp. Med. 179:1317–1330; Ajmani et al., 1995, J. Exp. Med. 181:2049–2058). Although molecular alterations have been shown to be closely associated with apoptosis, little is known about their precise role in the process of apoptotic cell death.

The molecular alterations in apoptosis have not only been observed in cell membranes and the nucleus, but also in mitochondria. Mitochondrial DNA may not be fragmented in the apoptotic cell, while its nuclear DNA has been cleaved into fragments by endonucleases (Murgia et al., 1992, J. Biol. Chem. 267:10939–10941; Tepper and Studzinski, 1992, Cancer Res. 52:3384–3390). However, the abnormal ultrastructure of mitochondria and a reduction in mitochondrial membrane potential have been found in cells undergoing apoptosis (Vayssiere et al., 1994, Proc. Natl. Acad. Sci. U.S.A. 91:11752–11756; Zamzami et al., 1995, J. Exp. Med. 181:1661–11672; Steller, 1995, Science 267:1445–1449). The localization of Bcl-2 to mitochondrial membranes has implicated some functional influence of mitochondria on apoptosis although the Bcl-2 gene product is also found in the nuclear envelope and endoplasmic reticulum (Hockenbery et al., 1990, Nature 248:334–346; Krajewski et al., 1993, Cancer Res. 53:4701–4714). Using a human fibroblast cell line that lacks mitochondrial DNA, Jacobson et al., (1993, Nature 361:365–369) reported that neither the induction of apoptosis by growth factor withdrawal nor the antiapoptosis effect of Bcl-2 appears to depend on the activity of mitochondrial respiratory chain. Overexpression of Bcl-2, however, does enhance the mitochondrial membrane potential and rescues cells from apoptotic cell death (Hennet et al., 1993, Cancer Res. 53:1456–1460). Consistent with these findings, Zamzami et al. (1995, J. Exp. Med. 181:1661–1672) have recently shown that a reduction in mitochondrial membrane potential is an early irreversible event of lymphocyte apoptosis in vivo, and that some pharmaceutical agents capable of blocking early signaling pathways for apoptosis efficiently stabilize the values of mitochondrial membrane potential. These data have suggested the involvement of mitochondrial components in apoptotic cell death.

To identify the molecular markers for apoptotic cells, monoclonal antibodies were developed by immunizing mice with dying Jurkat cells. An antibody, designated anti-7A6, was found to react preferentially with cells undergoing apoptosis and not with normal cells. The antibody-defined molecule is a 38 kD protein localized to the membrane of mitochondria.

The monoclonal antibody can be used to distinguish apoptotic cells from normal cells, study the molecular mechanisms of apoptosis and diagnose samples from apoptosis-related diseases, to monitor the efficacy of therapeutic regimens, and to identify novel agents which induce or inhibit apoptosis. Reference is made to the article by Thompson, (1995, Science 267:1456–1462) which describes in detail the role of apoptosis in the pathogenesis and treatment of disease.

SUMMARY OF THE INVENTION

The present invention features monoclonal antibodies, or immunoreactive fragments thereof, which distinguish between normal and apoptotic cells in a human cell population. The monoclonal antibodies specifically bind to an antigen on the membrane of mitochondria in apoptotic cells. The antigen, which is a 38 kD protein is detectable in cells undergoing apoptosis and undetectable in normal cells.

The monoclonal antibodies of the invention are preferably murine, but can also be derived from other mammalian species including but not limited to human and rat, or combinations thereof. In a preferred embodiment, the antibody is produced from a hybrid cell line developed from Balb/c mice immunized with apoptotic Jurkat cells. The hybrid cell line has been deposited with the American Type Culture Collection, and is assigned A.T.C.C. No. HB 12065.

The monoclonal antibodies of the invention recognize a novel antigen (7A6), and bind specifically to an epitope of this antigen on the mitochondrial membrane in apoptotic cells. These antibodies or fragments thereof can be used in methods to distinguish between normal and apoptotic cells in a biological sample, for example, in human hemopoietic cell populations, including peripheral blood lymphocytes, T cell lines, B cell lines, histiocytic cell lines and promyeloid cell lines. Further, due to this selectivity of the antibodies a method for detecting and measuring cells undergoing apoptosis is also provided.

Other objects, features and advantages of the invention will be apparent when the detailed description of the preferred embodiments are considered in conjunction with the drawings which should be construed in an illustrative and not limiting sense as follows:

BRIEF DESCRIPTION OF THE DRAWINGS

FIG. 6C shows mitochondria from apoptotic cells stained with anti-7A6 (×35,000 original magnification). FIG. 6D shows sample as in FIG. 6C but examined under a higher magnification (×72,000). The gold particles observed were localized to the surface of inner membrane (arrows) of the mitochondrion (m). FIG. 6E shows mitochondria from normal cells stained with anti-7A6; and FIG. 6F shows mitochondria from apoptotic cells stained with an isotype matched control antibody. The bar in the figures represent 0.5μ.

FIGS. 7A–D are graphic illustrations of the flow cytometric analyses of peripheral blood lymphocytes from an HIV-infected donor. FIG. 7A depicts cytometric analysis using a control antibody of HIV-infected cells activated with CD3. FIG. 7B depicts cytometric analysis using a control antibody of HIV-infected cells activated with PMA. FIG. 7C depicts cytometric analysis using an anti-7A6 of HIV-infected cells activated with CD3. FIG. 7D depicts cytometric analysis using anti-7A6 of HIV-infected cells activated with PMA.

DESCRIPTION OF THE PREFERRED EMBODIMENTS

Figure 1A:
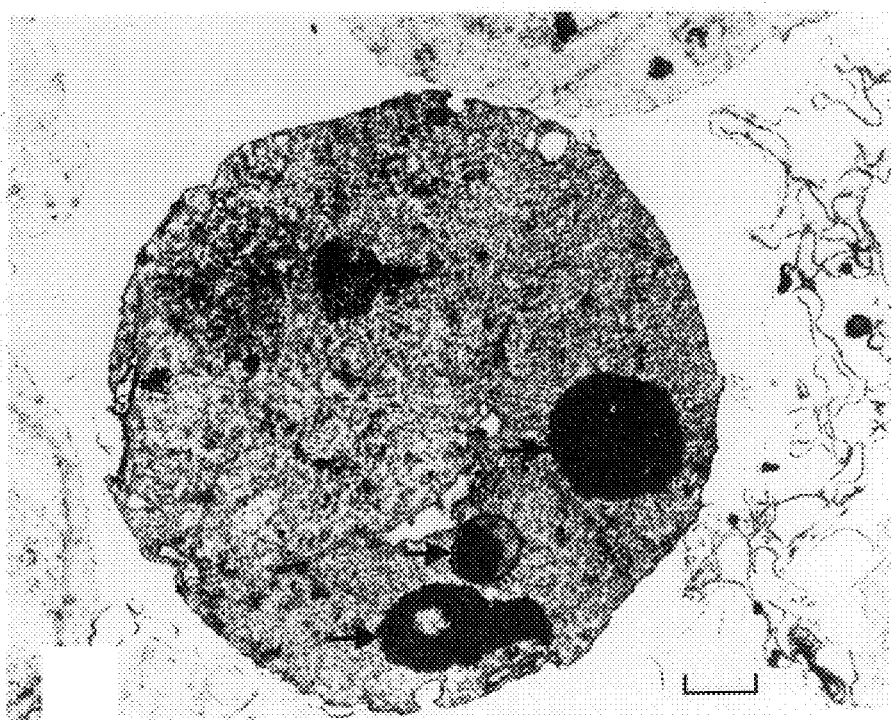
FIGS. 1A and 1B show electron micrographs of apoptotic Jurkat cells induced by Ara-C (1-β-D-arabinofuranosyl cytosine). Jurkat cells were incubated in the presence (FIG. 1A) or absence of 10 μM Ara-C (FIG. 1B) in RPMI 1640 medium supplemented with 10% fetal bovine serum. Both cells were examined by transmission electron microscope at the same magnifications (×18,000). Arrows indicate the structure of apoptotic bodies. The bars in the figures represent 1μ.

A monoclonal antibody, designated anti-7A6, that defines a unique epitope exposed on apoptotic cells is provided by the invention. As analyzed by flow cytometry, anti-7A6 fails to stain normal, digitonin-permeabilized human peripheral blood lymphocytes and a number of human cell lines tested. In contrast, the antibody labels cells undergoing apoptosis regardless of whether the cells have been permeabilized by digitonin or not. ELISA and immunoblot using cell lysates prepared in Triton X-100 lysis buffer have also indicated that anti-7A6 reacts with apoptotic Jurkat cells but not with normal cells. The antigen defined by anti-7A6 is a 38 kD protein localized to the membrane of mitochondria. These findings indicate that the 7A6 is a novel epitope exposed on cells undergoing apoptosis.

An increasing number of molecular events have been shown to regulate cell death by apoptosis. Induction of apoptosis is believed to activate endonucleases which are responsible for the degradation of DNA into nucleosomesize fragments (Duke et al., 1983, Proc. Natl. Acad. Sci. U.S.A. 80:6361–6365; Barry and Eastman, 1993, Arch. Biochem. Biophys. 300:440–450; Peitsch et al., 1993, EMBO J. 12:371–377). A triplet of nuclease proteins (NP42–50) have recently been identified, which is activated in Jurkat cells undergoing apoptosis and appears to be distinguishable from DNase I and DNase II by its molecular characteristics and enzymatic requirements (Zhang et al., 1995, Cell.Immunol. 165:161–167). In addition to the nucleus disrupted in apoptosis, mitochondria have also been found to be the cellular target with damages beginning at the early stage of apoptosis although the fragmentation of mitochondrial DNA may not be required for cell undergoing apoptosis (Murgia et al., 1992, J. Biol. Chem. 267:10939–10941; Tepper and Studzinski, 1992, Cancer Res. 52:3384–3390; Yoneda et al., 1995, Biochem. Biophys. Res. Comm. 209:723–729). Indeed, some apoptosis-inducing agents have been shown to cause the loss of mitochondrial integrity and its functional failure leading to cell death (Vukmanovic et al., 1991, Eur. J. Immunol. 21:419–424; Hennet et al., 1993, Biochem. J. 289:587–592). In contrast, overexertion of Bcl-2, a protein that enhances cell survival by blocking pathways for apoptosis, has shown to increase values of mitochondrial membrane potential in transfectant cells and protects mitochondrial membrane potential loss by apoptosis (Hennet et al., 1993, Cancer Res. 53:1456–1460; Smets et al., 1994, Blood 5:1613–1619). The specific localization of the 7A6 antigen to the mitochondrial membrane and its restricted expression on apoptotic cells indicates that the 7A6 antigen is involved in the molecular cascade of apoptosis.

The expression of 7A6 antigen is preferentially detected on apoptotic cells, but not on the normal cell surface or on digitonin-permeabilized cells. Moreover, activation of Jurkat cells by mitogens has no effects on the expression of 7A6 antigen. Flow cytometric profiles have also shown the 7A6 antigen to be detected at the early stage of apoptosis, further indicating that the expression of 7A6 antigen represents an early event of apoptosis rather than a final product of dead cells. Using monoclonal antibody techniques, Rotello et al., (1994, Development 120:1421–1431) have reported that cells dying by apoptosis during chicken embryonic development expressed specific antigens termed apogens although some of these antigens have been found to be expressed on necrotic cells as well (Fernandez et al., 1994, Proc. Natl. Acad. Sci. U.S.A. 91:8641–8645). Interestingly, several intracellular molecules within normal cells have been shown to be exposed on the cell surface during apoptosis (Casciola-Rosen et al., 1994, J. Exp. Med. 179:1317–1330; Koopman et al., 1994, Blood 184:1415–1420). In contrast, the 7A6 is unlikely to be a conventional intracellular protein which is expressed on the cell surface of apoptotic cells since it cannot be detected in digitonin-permeablized normal cells by flow cytometry or in lysates of these cells by immunoblots.

The methods and materials used to produce the monoclonal antibodies and define the antigen of the invention are described in detail below. In summary, a panel of monoclonal antibodies was raised against dying cells by immunizing mice with apoptotic Jurkat cells. One of these antibodies, anti-7A6, was found to react with apoptotic cells. As determined by flow cytometry and ELISA, no reactivity of anti-7A6 was observed in normal or digitonin-permeabilized human peripheral blood lymphocytes and all lymphoid cell lines tested. The antibody, however, strongly reacted with these cells when they were induced to undergo apoptosis by irradiation or treatment with apoptosis-inducing agents. Cell sorting and DNA fragmentation experiments revealed that 7A6+ cells, but not 7A6− cells, had apparent DNA fragments characteristic of cells undergoing apoptosis. By immunoblot under reducing conditions anti-7A6 detected a 38 kD protein band in the cell lysates prepared from apoptotic cells. Immunoelectron microscopy showed the 7A6 antigen to be localized to the membrane of mitochondria in apoptotic Jurkat cells. These results indicate that anti-7A6 defines a novel epitope on the mitochondrial membrane protein which is exposed on cells undergoing apoptosis, indicating that the 7A6 molecule may be involved in the molecular cascade of apoptotic cell death.

The methods described herein can be used to generate additional monoclonal antibodies with the characteristics of the anti-7A6 antibody described in the examples set forth below, or by methods well-known to those skilled in the art. Screening procedures to identify antibodies with the desired characteristics are also described herein. In addition, the identification of antibodies and immunoreactive fragments thereof within the scope of the invention can be accomplished using standard competitive binding assays known to the skilled artisan using the anti-7A6 antibody provided by the hybrid cell line designated by ATCC Accession No. HB12065.

Also included within the scope of the present invention are antibody fragments and derivatives which comprise at least the functional portion of the antigen binding domain of an anti-7A6 antibody molecule.

Antibody fragments which contain the binding domain of the molecule can be generated by known techniques. For example, such fragments include, but are not limited to: The F(ab')2 fragment which can be produced by pepsin digestion of the antibody molecule; the Fab' fragments which can be generated by reducing the disulfide bridges of the F(ab')2 fragment; and the Fab fragments which can be generated by treating the antibody molecule with papain and a reducing agent. See, e.g., National Institutes of Health, 1 Current Protocols In Immunology, Coligan et al., ed. 2.8, 2.10 (Wiley Interscience, 1991). Antibody fragments also include Fv fragments, i.e. antibody products within which there are not constant region amino acid residues. Such fragments can be produced, for example as described in U.S. Pat. No. 41642,334.

Monoclonal Antibody Development Antibodies and Other Reagents

Monoclonal antibody anti-7A6 was screened and cloned from a hybridoma generated by fusing mouse myeloma P3-X63-Ag.8.653 (Kearney et al. 1979, J. Immunol. 123:1548–1550) with splenocytes from a mouse immunized with whole apoptotic Jurkat cells. Female Balb/c mice were immunized 4 times, either subcutaneously or intraperitoneally, at 3–4 week intervals with Jurkat cells that had been induced to undergo apoptosis by 1-β-D-arabinofuranosyl cytosine (Ara-C), an anti-metabolite agent. Three days before cell fusion, the mouse was boosted by intraperitoneal injection with the cellular antigens (apoptotic Jurkat cells). Splenocytes from the immunized mouse were fused with myeloma cells using polyethylene glycol by the method previously described (Köhler and Milstein, 1975, Nature 256:495–497). Anti-7A6 was screened against cells undergoing apoptosis. It was shown to be an IgG1 subclass using commercial antibody isotyping reagents (Amersham Life Science, Arlington Heights, Ill.). Ascites for anti-7A6 were produced in mice and the antibody was purified from ascites fluid by protein A affinity column (Pharmacia, Piscataway, N.J.).

Anti-7C11 (IgM) is a mouse monoclonal antibody reactive with the CD95 (Fas/Apo-1) antigen (Robertson et al., 1995, Leuk. Lymphoma 17:51–58) and was provided by Dr. Robertson. Affinity purified goat anti-mouse IgG-FITC conjugate for flow cytometry and goat anti-mouse IgG-gold conjugate for electron microscopy were obtained from Jackson ImmunoResearch laboratories (West Grove, Pa.) and from Amersham Life Science (Arlington Heights, Ill.), respectively. Monoclonal mouse anti-α-tubulin (IgG1), Ara-C and all other chemical reagents were obtained from Sigma Immunochemicals (St.Louis, Mo.) unless where indicated.

Cell Culture and Induction of Apoptosis

Human T cell Lines (Jurkat, CEM, Molt-4 and HT-102), B cell lines (Raji, Daudi and Ramos), histiocytic cell line (U-937) and promyeloid cell line (HL-60) were used in this study. All cell lines were maintained in RPMI 1640 medium supplemented with 10% fetal bovine serum, 0.45 mM pyruvic acid and 2 mM L-glutamine. Human peripheral blood lymphocytes were isolated from healthy donors or from HIV-infected donors by density gradient centrifugation over Ficoll-Hypaque (Pharmacia, Piscataway, N.J.).

For induction of apoptosis in cell culture, Jurkat cells were treated with Ara-C or anti-CD95 (Fas/Apo-1) as previously described (Zhang et al., 1995, Cell. Immunol. 165:161–167). Induction of apoptosis in human peripheral blood lymphocyte, Jurkat cell and all other cell lines was also done by γ-irradiation followed by incubation overnight at 37° C. The radiation doses varied among cell from 1000–3000 Rads using a GammaCell-1000 with a $^{137}$Cs source (Atomic Energy of Canada Limited., ON, Canada). Apoptotic cell death by irradiation or apoptosis-inducing agents was confirmed by analysis of DNA fragmentation and cell morphology.

Cell Permeabilization by Digitonin and Immunofluorescence Staining for Flow Cytometry Human peripheral blood lymphocytes or cell lines were permeabilized by the previously described method (Fiskum et al., 1980, Proc. Natl. Acad. Sci. U.S.A. 77:3430–3434; Anderson et al., 1989, J. Immunol. 143:1899–1904) with minor modifications. Briefly, cells were fixed in 1% formalin in PBS for 20 min on ice, and washed twice with PBS. The cells were then permeabilized by incubation on ice for 5 min with digitonin (Aldrich, Milwaukee, Wis.). A stock solution of 10 mg ml$^{-1}$ of digitonin was prepared by dissolving in dimethylsulfoxide and a final concentration of 10 μg ml$^{-1}$ diluted from the stock solution with PBS was used for cell permeabilization. The permeabilization of cells by digitonin was confirmed by the uptake of Trypan blue. Following permeabilization, the cells were washed and resuspended in PBS for immunofluorescence staining.

Cells with or without digitonin-permeabilization were labeled with antibodies for flow cytometry by an indirect immunofluorescence assay. After incubation for 40 min on ice with 100 μl of monoclonal antibody supernatant or diluted ascites, cells (approximately 1×10$^6$ cells/sample) were washed 3 times with PBS containing 0.1% bovine serum albumin and 0.01% NaN3. Following a further incubation for 40 min with affinity purified goat anti-mouse IgG-FITC conjugate (1:500), the cells were washed 3 times in the buffer above, and fixed in 1% formalin in PBS for flow cytometric analysis.

For immunofluorescence labeling for cell sorting, a mixture of 2×10$^7$ normal Jurkat cells and 4×10$^7$ Ara-C treated Jurkat cells was stained with anti-7A6 followed by goat anti-mouse IgG-FITC conjugate. After incubation and washes, the cells were pelleted and then resuspended in PBS instead of fixation in 1%. Formalin. Using an Epics V cell sorter, the sample was sorted for 7A6 -positive and negative cell populations. Purity of separated 7A6 positive and negative cells was greater than 98% as determined by flow cytometry and the viability of postsorted cell subpopulations was examined by Trypan blue exclusion. The 7A6 -positive or negative cells were then washed, pelleted and used for the DNA fragmentation assay.

Preparation of Cell Lysate

Normal or apoptotic cells induced by γ-irradiation or Ara-C treated Jurkat cells were harvested from cell cultures and washed twice with PBS by centrifugation. The cell pellets were solubilized in a lysis buffer containing 0.5% Triton X-100, 50 mM Tris-HCl, pH 7.6, 140 mM NaCl, 5 mM EDTA, 1 mM phenylmethylsulfonyl fluoride and 2 μml$^{-1}$ aprotinin. After incubation on ice for 40 min, the samples were centrifuged for 15 min at 14,000 rpm at 4° C. and supernatants were collected for ELISA and immunoblotting assays as described below.

ELISA for Detection of Antibody

An ELISA assay using cell lysates as the target antigens was performed by a modification of methods previously described (Cobbold and Waldmann, 1981, J. Immunol. Meth. 44:125–133). ELISA plates were prepared by attaching cellular proteins onto the wells of flatbottomed, polystyrene Falcon microtest plates (Becton Dickinson Labware, Lincoln Park, N.J.) using poly-L-lysine and glutaraldehyde. Upon treatment with poly-L-lysine for 1 hr, plates were coated with 50 μl of diluted cell lysates equivalent to 2.5×10$^5$ cells per well. Following incubation at room temperature for 1 hr, the plates were filled with 50 μl of 0.2% fresh-prepared glutaraldehyde and incubated for 15 min. Plates were emptied and washed once with PBS. A blocking buffer containing 100 mM glycine and 0.1% bovine serum albumin was added and incubated for 30 min. The plates were then filled with 0.2% gelatin and incubated at 4° C. overnight. All solutions used in this assay were prepared in regular PBS, pH 7.4. The dilution of test antibodies and goat anti-mouse IgG-peroxidase (Jackson ImmunoResearch Laboratories, West Grove, Pa.) was made in 10% normal goat serum in PBS.

For the ELISA test, monoclonal antibodies with various dilutions (25 μl/well) were added to precoated plates, and each antibody dilution was tested in triplicate. A mouse anti-α-tubulin and an isotype matched non-reactive antibody were used as the positive and negative controls, respectively. After incubation for 1 hr at room temperature, plates were washed 3 times with 0.1% gelatin solution and incubated for 10 min with 10% normal goat serum to block nonspecific binding. The plates were then incubated for 30 min with goat anti-mouse IgG-peroxidase. Following washes with 0.05% Tween-20 in PBS, the enzymatic reaction was developed by incubation of the plates for 45 min at room temperature with substrate solution (30 mg ortho-phenylenediamine dissolved in 10 ml of 100 mM citrate buffer, pH 4.5, and 4 μl of 30% hydrogen peroxide), and stopped by adding 50 μl of 2.5M sulfuric acid to each well. The plates were read at 492 nM using an automatic ELISA reader (Dynatech Laboratories, Inc., Alexandria, Va.).

Immunoblotting Assay

Cell lysates prepared from normal or apoptotic cells were separated on SDS-PAGE and transferred onto a nitrocellose membrane (Schleicher & Schuell, Keene, N.H.). After incubation with 3% bovine serum albumin in PBS to block nonspecific binding sites, the membrane was incubated with anti-7A6 followed by protein-G-peroxidase conjugate (Bio-Rad, Richmond, Calif.). The membrane was washed 4 times with Tris-HCI buffer, pH 7.6, containing 0.05% Tween-20 and 0.1% gelatin following each incubation. Immunoblots were detected by an enhanced chemiluminescence (Amershan, Arlington Heights, Ill.) according to the manufacturer's instruction.

Isolation of Mitochondria

Normal or apoptotic Jurkat cells induced by Ara-C were washed and resuspended in an ice-cold buffer containing 10 mM HEPES, pH 7.5, 1.5 mM MgCl$_2$, 5 mM KCl and 250 mM sucrose, and then disrupted by Dounce homogenization using a type-B pestle (Wheaton, Millville, N.J.). Post-nuclear supernatants containing cytoplasmic organelles were collected by centrifugation for 5 min at 1300 g. Pellets were resuspended in 250 mM sucrose solution and centrifuged to collect supernatant again. The supernatants from both centrifugations were pooled and used for the isolation of mitochondria.

Mitochondria were isolated from the post-nuclear supernatants using a Percoll-metrizamide gradient described by Storrie and Madden (1990, In Methods in Enzymology, Vol. 182:203–225). Briefly, a discontinuous density gradient was prepared in a centrifuge tube by loading a 35% metrizamide on the bottom layer a 17% metrizamide on the second layer followed by 6% Percoll. All gradient solutions were prepared in 250 mM sucrose. Post-nuclear supernatants containing cytoplasmic organelles were loaded on the top of the Percoll layer. Following centrifugation for 20 min at 20,000 rpm at 4° C., mitochondria were enriched at the interface between 17% and 35% metrizamide layers. The resulting mitochondria were washed and pelleted by centrifugation.

Immunogold staining for electron microscopy

Normal or Ara-C treated Jurkat cells were fixed and prepared for frozen sections as previously described (Griffiths and Hoppeler, 1986, J. Histochem. Cytochem. 34:1389–1398). The sections were labeled with anti-7A6 or an isotype-matched control antibody followed by goat anti-mouse IgG conjugated to 10 nM gold particles. Following washes and treatments, the samples were examined by electron microscope.

Cells or isolated mitochondria from normal and Ara-C treated Jurkat cells were also examined for immunogold particles by electron microscope using a pre-embedding labeling assay. After fixed and permeabilized by digitonin as described above, cells or isolated mitochondria were stained with anti-7A6 or control antibody as a first-stage reagent, and goat anti-mouse IgG-gold conjugate as the second reagent. Following the incubation and washes, the samples were pelleted by centrifugation and embedded in gelatin medium. The samples were sectioned with an ultramicrotome and examined by electron microscope.

Reactivity of anti-7A6 with apoptotic cells induced by irradiation, treatment with Ara-C or anti-CD95 (Fas/Apo-1), and normal cells It was found that anti-7A6 reacts with apoptotic cells induced by irradiation, treatment with Ara-C or anti-CD95 (Fas/Apo-1), but fails to react with normal cells.

Figure 1B:
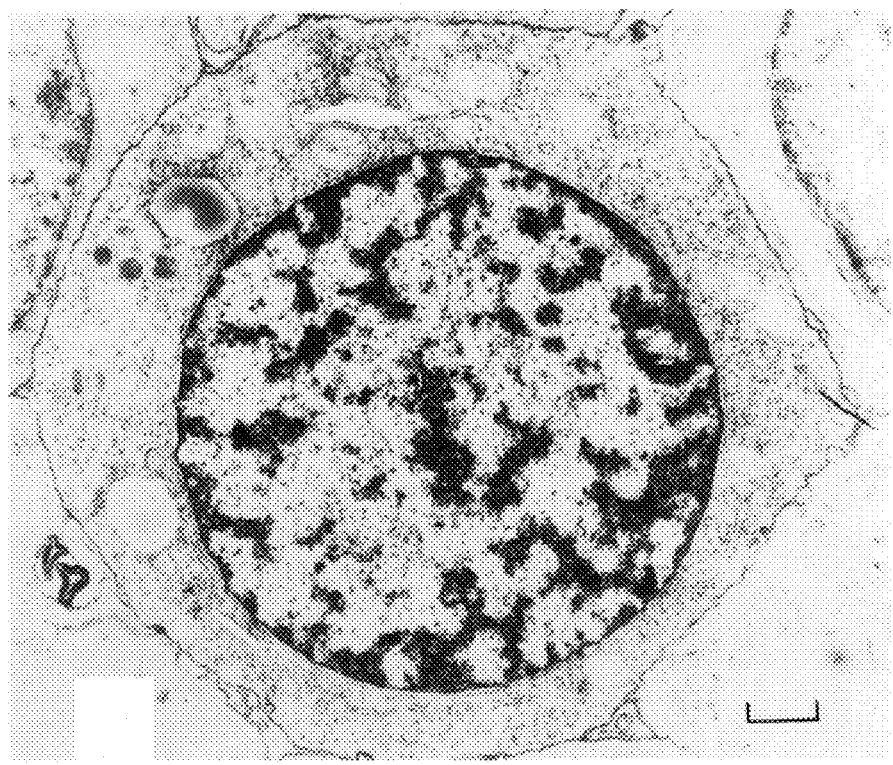

Anti-7A6, an antibody of mouse IgG1 isotype, was screened and cloned from a hybridoma which was derived from mouse splenocytes immunized with Ara-C treated Jurkat cells, a tumor cell line. Ara-C is an anti-metabolite agent which effectively induces Jurkat cells to undergo apoptotic cell death in micromolar concentrations. When cultured in the presence of Ara-C, Jurkat cells exhibited the cleavage of DNA into internucleosomal fragments characteristic of apoptosis. Morphologically, these cells displayed a loss of surface microvilli, cytoplasmic condensation, nuclear disruption, and apoptotic bodies (FIG. 1A). In contrast to normal cells, the cell dying by Ara-C inducing apoptosis shrinked remarkably and its size was reduced by 20–30%, as determined by electron microscope using the same magnification (FIG. 1).

Figure 2A:
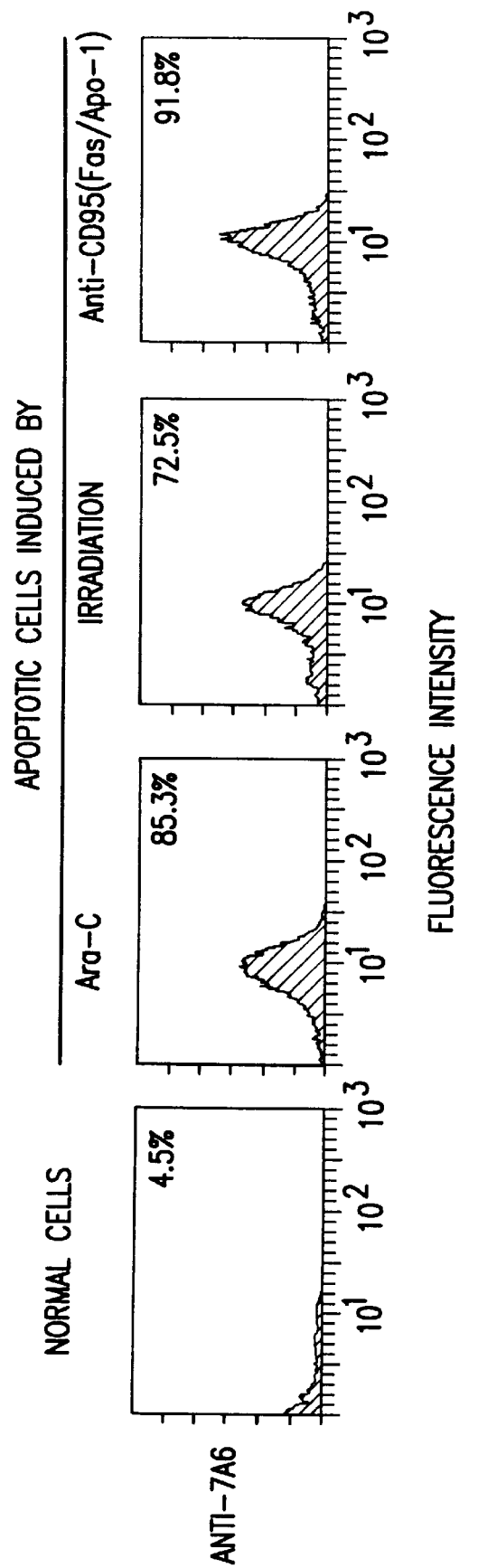
FIGS. 2A and 2B are graphic illustrations of the flow cytometric analysis of anti-7A6 on normal and apoptotic Jurkat cells. Jurkat cells were induced to undergo apoptosis by γ-irradiation, treatment with Ara-C or anti-CD95 (Fas/Apo-1). The apoptotic or normal Jurkat cells were not permeabilized (FIG. 2A) or were permeabilized by digitonin (FIG. 2B) before being labeled with immunofluorescence for flow cytometry. The percentage of positive cells is indicated in each profile.
Figure 2B:
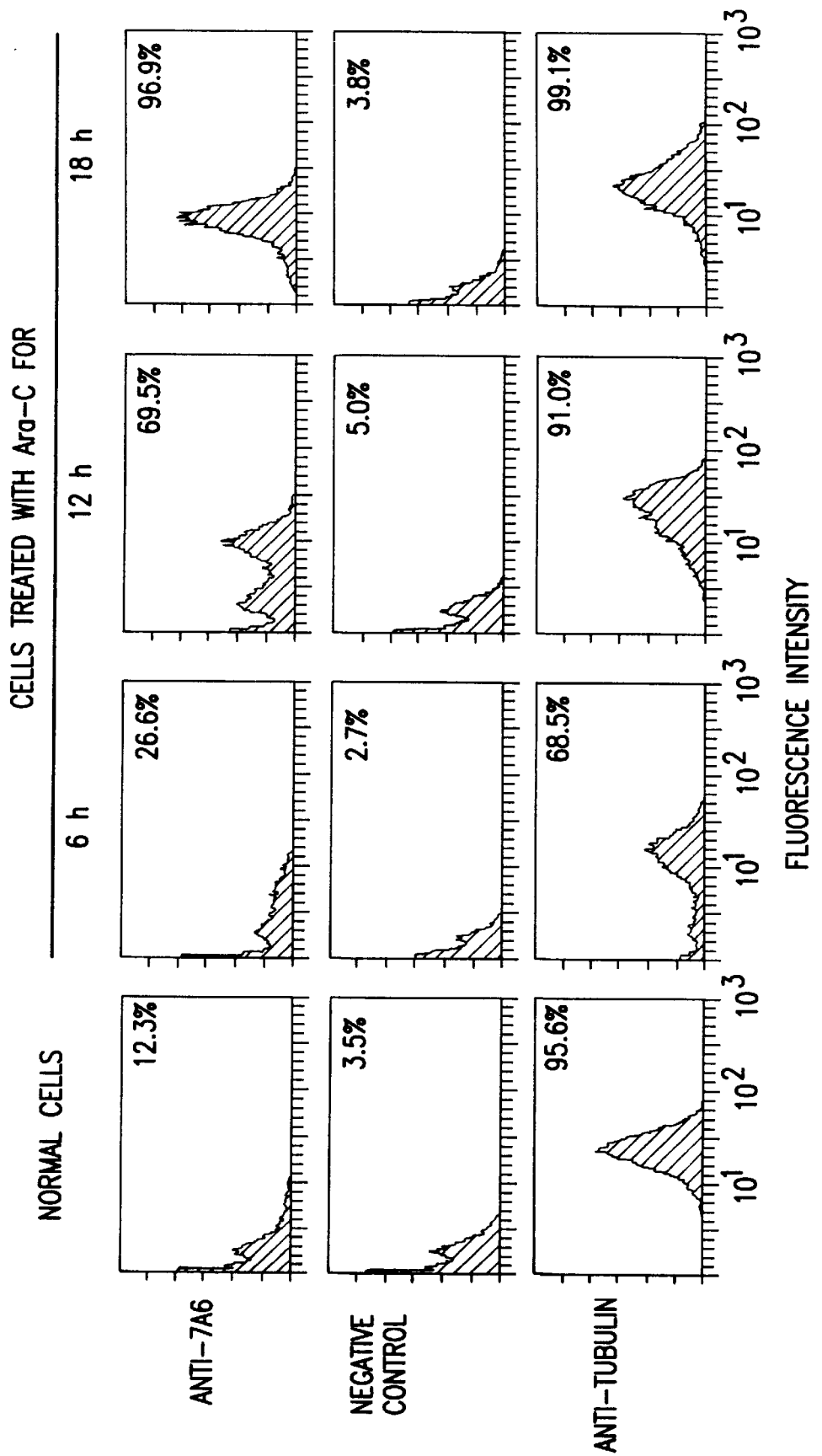

The reactivity of anti-7A6 with Jurkat cells was initially tested by flow cytometry using an indirect fluorescence staining technique. FIG. 2 represents flow cytometric profiles of the 7A6 antigen on unpermeabilized or digitonin permeabilized normal and apoptotic Jurkat cells. As shown in FIG. 2A, no reactivity of anti-7A6 was detected in normal Jurkat cells. In contrast, anti-7A6 was found to stain Jurkat cells undergoing apoptosis induced by γ-irradiation, treatment with Ara-C or anti-CD95 (Fas/Apo-1) even when the cells were not permeabilized by digitonin. This antibody, however, failed to label Jurkat cells activated by mitogens including Con-A or PMA. To further confirm the reactivity of anti-7A6, normal or apoptotic Jurkat cells were permeabilized by digitonin, stained with antibodies, followed by immunofluorescence flow cytometry (FIG. 2B). Compared to the isotype-matched control antibody which showed no reactivity with either normal or apoptotic Jurkat cells, anti-7A6 reacted with Ara-C treated Jurkat cells in a time course dependent manner, but not with untreated Jurkat cells even when the cells had been permeabilized by digitonin. As expected, monoclonal anti-tubulin stained both normal and apoptotic Jurkat cells following digitonin permeabilization. See FIG. 2.

The ability of anti-7A6 to detect and quantify apoptotic cells in HIV-infected peripheral blood lymphocytes was also tested. PBLs (peripheral blood lymphocytes) from an infected donor were either treated with CD3 or PMA, agents which induce T cell activation. Cytometric analyses were then carried out on the activated cells using a control antibody or anti-7A6. Compared to the control, anti-7A6 was found to detect and quantify HIV-infected PBLs undergoing apoptosis. See FIGS. 7A–7D.

The reactivity of anti-7A6 with human peripheral blood lymphocytes and cell lines is summarized in Table 1 below. As determined by flow cytometry, anti-7A6 failed to stain normal human peripheral blood lymphocytes and all cell lines tested regardless of whether the cells were permeabilized by digitonin or not. When cells were induced to undergo apoptosis by γ-irradiation or Ara-C treatment, however, anti-7A6 reacted widely with these cells although the percentage of 7A6-positive cells varied in different cell lines.

TABLE 1

Reactivity of anti-7A6 with human hemopoietic cells*

| CELL TYPE | NORMAL CELLS UNPERMEABILIZED | NORMAL CELLS PERMEABILIZED | APOPTOTIC CELLS INDUCED BY γ-IRRADATION |
|---|---|---|---|
| PERIPHERAL BLOOD LYMPHOCYTES | − | − | + |
| T CELL LINE: JURKAT | − | − | ++ |
| T CELL LINE: MOLT-4 | − | − | ++ |
| T CELL LINE: CEM | − | − | nt** |
| T CELL LINE: HUT-102 | − | − | nt |
| B CELL LINE: DAUDI | − | − | ++ |
| B CELL LINE: RAMOS | − | − | ++ |
| B CELL LINE: RAJI | − | − | nt |
| HISTIOCYTIC CELL LINE: U-937 | − | − | ++ |
| PROMYELOCYTIC CELL LINE: HL-60 | − | − | + |

*Normal cells with or without digitonin-permeabilization or apoptotic cells induced by γ-irradiation at 3000 Rads were labeled with anti-7A6 as described under Monoclonal Antibody Development. The reactivity of anti-7A6 was determined by flow cytometry.
The results are indicated as:
− = <5% positive cells above the background control;
+ = 10 . 50%; and
++ = >50%.
**nt = not tested.

Figure 3:
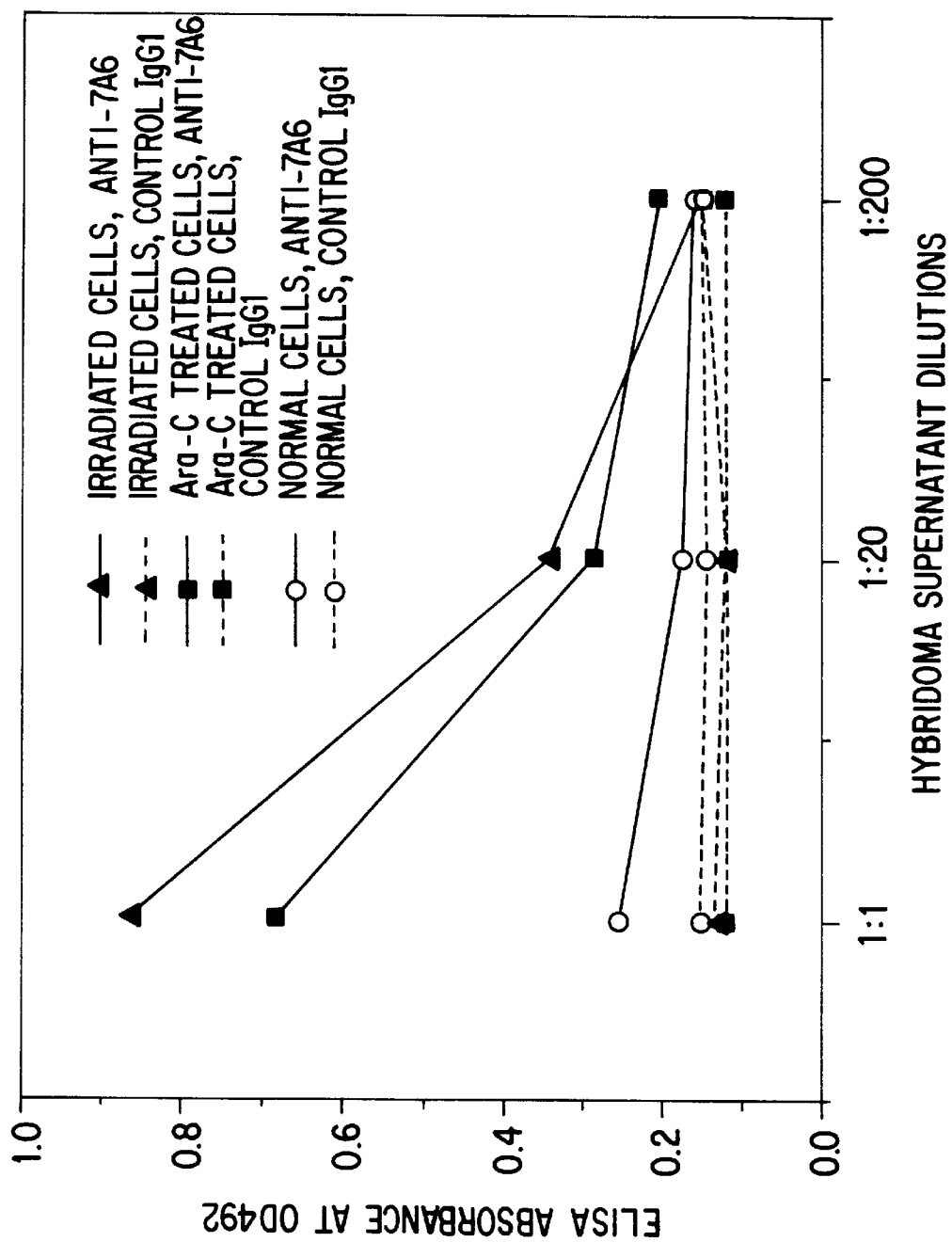
FIG. 3 is a graphic illustration of the ELISA test of cell lysates prepared from normal or apoptotic Jurkat cells. Cell lysates were prepared from normal or apoptotic Jurkat cells induced by γ-irradiation or Ara-C treatment, and precoated onto ELISA plates. The plates were incubated with anti-7A6 or an isotype-matched control antibody, followed by goat anti-mouse IgG-peroxidase conjugate. The enzymatic reaction was developed by orthophenylenediamine substrate and read at 492 nM using an ELISA reader.

To further test the specificity of anti-7A6, an ELISA was performed using cell lysates as target antigens (FIG. 3).

Anti-7A6 was found to react with lysates prepared from irradiated or Ara-C treated Jurkat cells but not with that of normal Jurkat cells. On the cell lysates from apoptotic Jurkat cells, the ELISA absorbance value for anti-7A6 were at least four-fold greater than that of isotype-matched negative control antibody, whereas the absorbance value for anti-7A6 on normal cell lysates was almost as low as that of negative control antibody. No significant difference was observed in the ELISA absorbance value for goat anti-tubulin on the cell lysates prepared from apoptotic and normal cells.

DNA Fragmentation Analysis

It was observed that purified 7A6+ cells but no 7A6− cells exhibited DNA fragmentation characteristic of cells undergoing apoptosis.

Figure 4A:
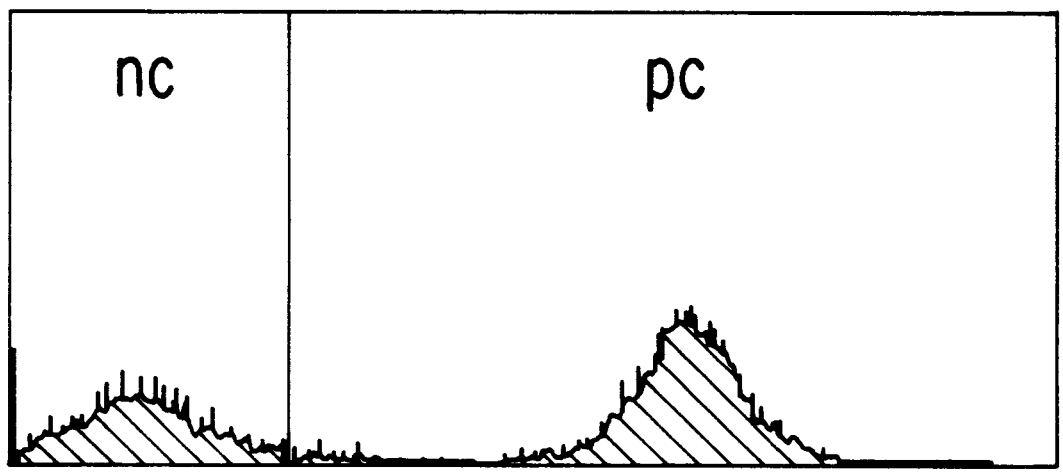
FIGS. 4A and 4B illustrate the DNA fragmentation assay on purified 7A6+ and 7A6– cells. Normal and Ara-C treated Jurkat cells were mixed and labeled for immunofluorescence with anti-7A6. The 7A6-positive (pc) and negative cells (nc) were then sorted by cell sorter (FIG. 4A). DNA was isolated from both cell populations and analyzed on 1.5% agarose gel electrophoresis as previously described (Zhang et al., 1995, Cell. Immunol. 165:161–167). Lane 1, a 100 bp DNA ladder as molecular weight markers; lane 2, DNA isolated from 7A6– cells; and lane 3, DNA from 7A6+ cells (FIG. 4B). The relative migration of DNA molecular weight standards (bp) is indicated.
Figure 4B:
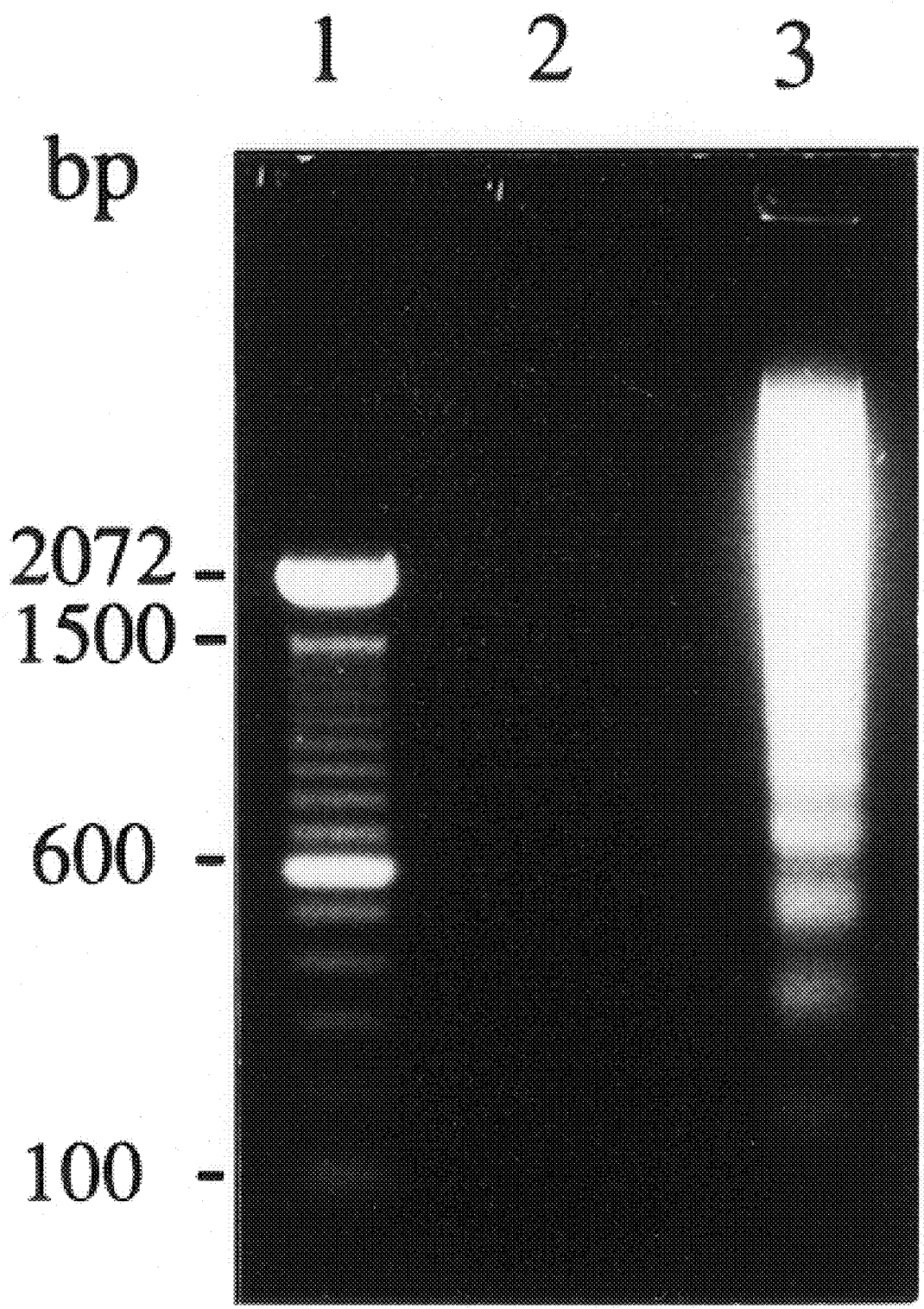

DNA fragmentation is a common feature of apoptosis and serves as a molecular marker for detection of cells dying by apoptosis. To test whether 7A6+ cells preferentially undergo DNA fragmentation, a specific cell purification using anti-7A6 and cell sorter was performed to sort for 7A6-positive and negative cells from a mixture of normal and Ara-C treated Jurkat cells (FIG. 4A). When stained with Trypan blue post-sorting, 7A6+ cells, but not 7A6− cells, lost the ability to exclude the dye. DNA was prepared from both cell populations and analyzed by agarose gel electrophoresis. As shown in FIG. 4B, cells positive for 7A6 were found to have a ladder pattern of DNA fragments on agarose gel. In contrast, no DNA fragmentation was detected in the 7A6 cell population.

Molecular Characteristics of the Antigen

Figure 5:
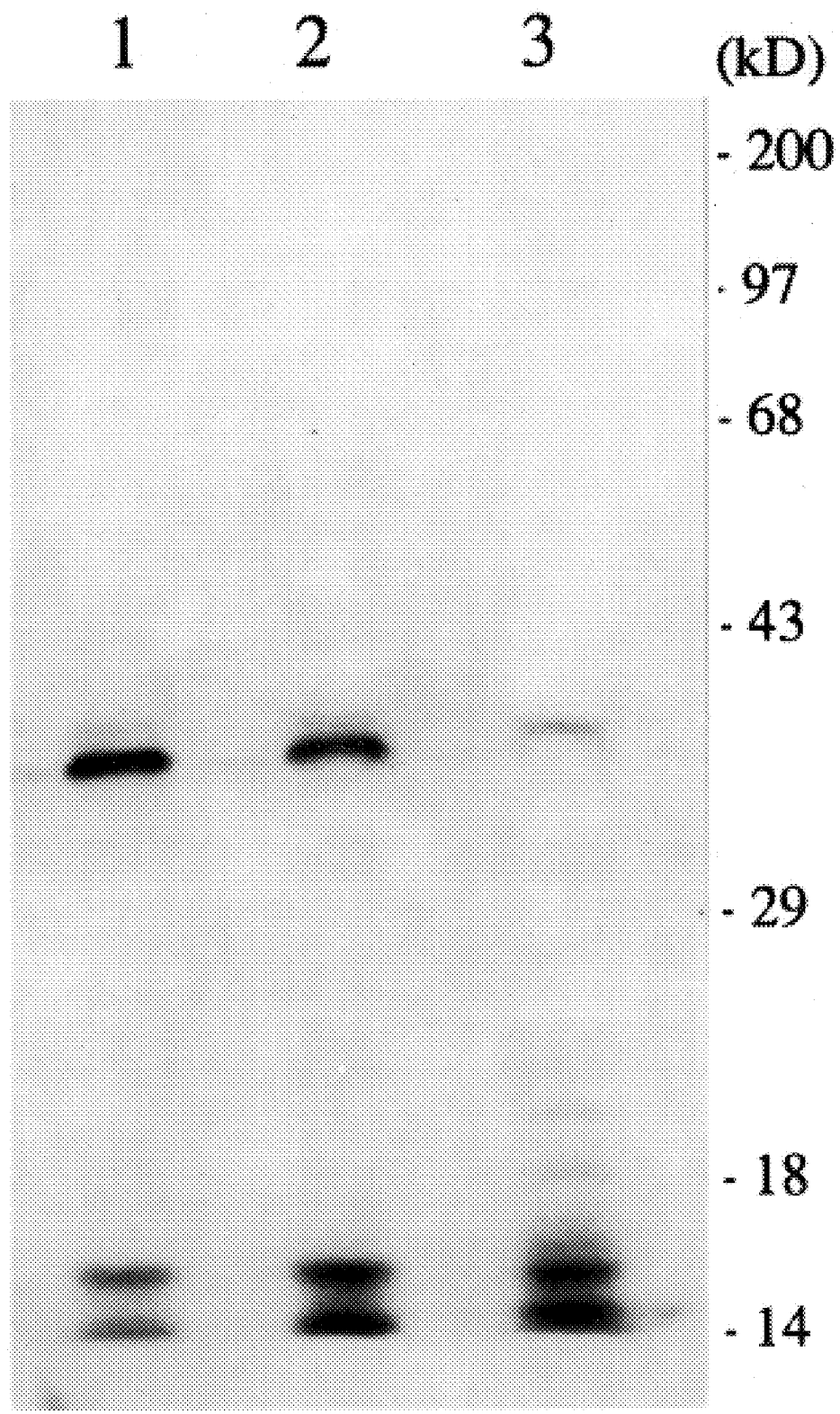
FIG. 5 is an Immunoblot of cell lysates by anti-7A6. Cell lysates were prepared from normal, irradiated or Ara-C treated Jurkat cells and subjected to SDS-PAGE containing 10% acrylamide gel under reducing conditions. Proteins were transferred onto the nitrocellose membrane, which was incubated with anti-7A6 followed by protein G-peroxidase. The blot was visualized by enhanced chemiluminescence technique. Lane 1, cell lysate from irradiated Jurkat cells; lane 2, cell lysate from Ara-C treated Jurkat cells; and lane 3, cell lysate from normal Jurkat cells. The relative migration of protein molecular weight standards is indicated.

Anti-7A6 detects a 38 kD protein in cell lysates prepared from apoptotic Jurkat cells. Immunoblotting assay using Jurkat cell lysates was performed to determine the molecular characteristics of 7A6 antigen. Cell lysates were prepared from normal, γ-irradiated or Ara-C treated Jurkat cells by solubilization in Triton X-100 lysis buffer. Proteins in the cell lysates were separated on SDS-polyacrylamide gel under reducing conditions and transferred onto nitrocellulose membrane which was blotted with anti-7A6. As shown in FIG. 5, anti-7A6 detected a specific protein band with molecular weight of approximately 38 kD in cell lysates prepared from apoptotic Jurkat cells induced by irradiation or Ara-C treatment (lanes 1 & 2). In contrast, the 38 kD protein band was not detected in the lysate from normal Jurkat cells under the identical experimental conditions (lane 3). Furthermore, anti-7A6 failed to detect the 38 kD protein band from normal cell lysates prepared in SDS-containing lysis buffer.

Figure 6A:
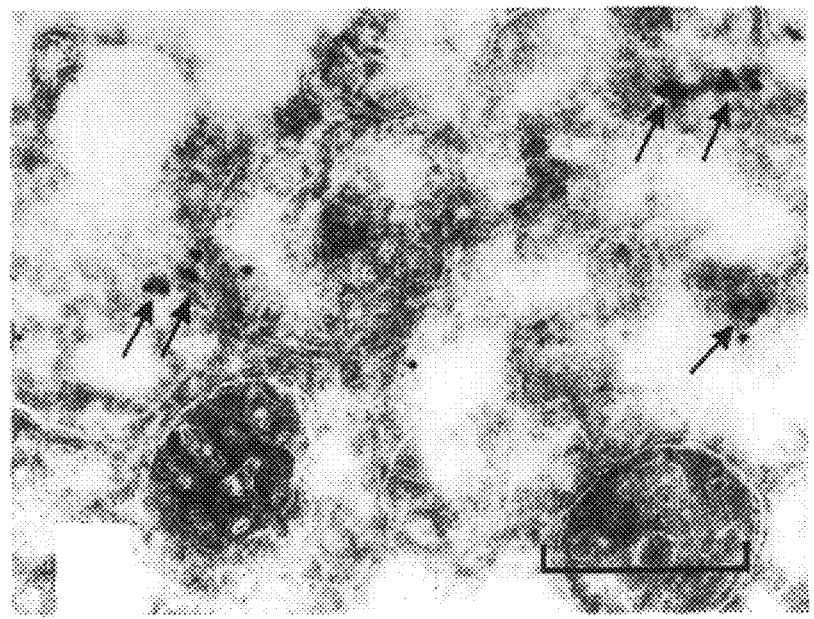
FIGS. 6A–F are electron micrographs showing localization of 7A6 antigens to the mitochondrial membrane. Cryosections prepared from Ara-C treated (FIG. 6A) or normal Jurkat cells (FIG. 6B) were labeled with anti-7A6 followed by immunogold conjugate, and examined by electron microscope. No label was observed in normal Jurkat cells whereas clusters of immunogold particles were found in Ara-C treated Jurkat cells (arrows). The reactivity of anti-7A6 was also tested on isolated mitochondria from normal and Ara-C treated Jurkat cells using Percoll-metrizamine gradient centrifugation (FIGS. 6C–F). The mitochondria were permeabilized by digitonin before being labeled with immunogold for electron microscopy.
Figure 6B:
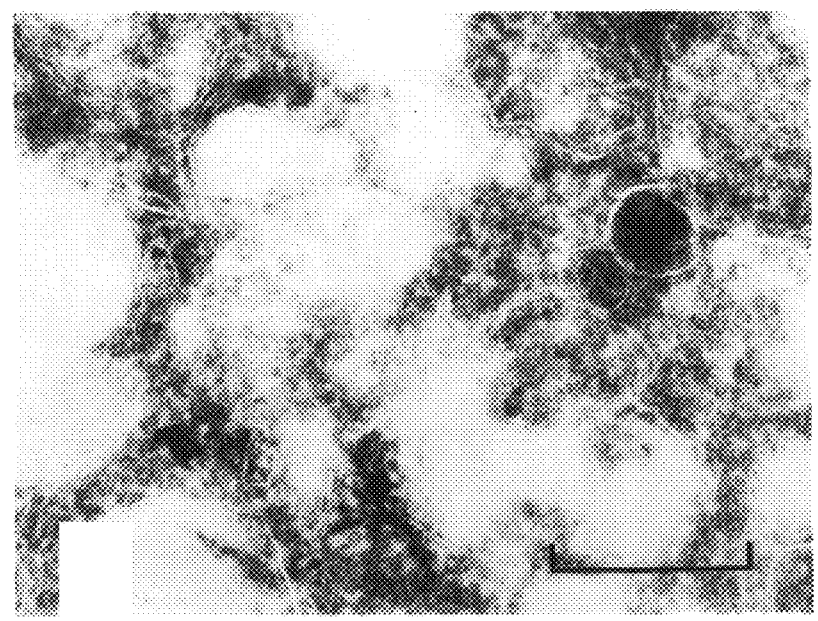
Figure 6C:
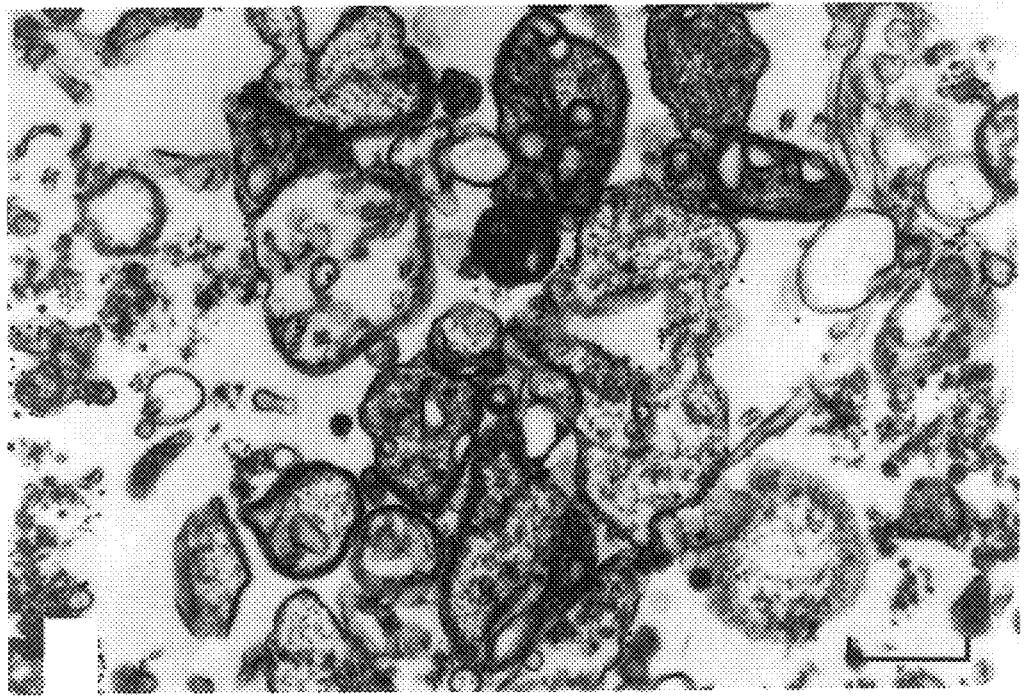
Figure 6D:
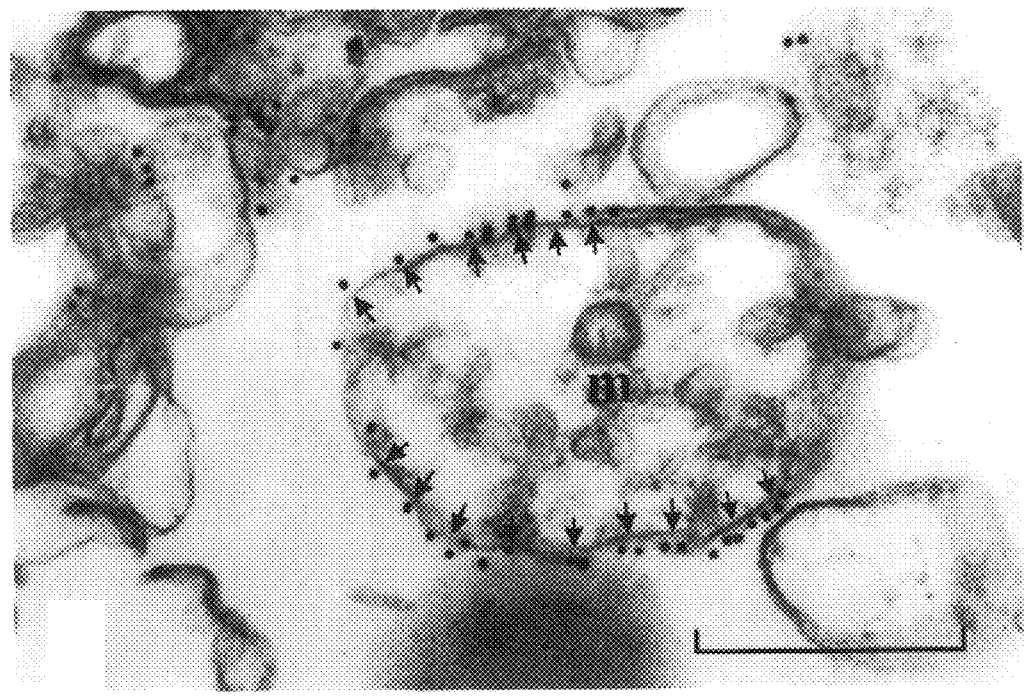
Figure 6E:
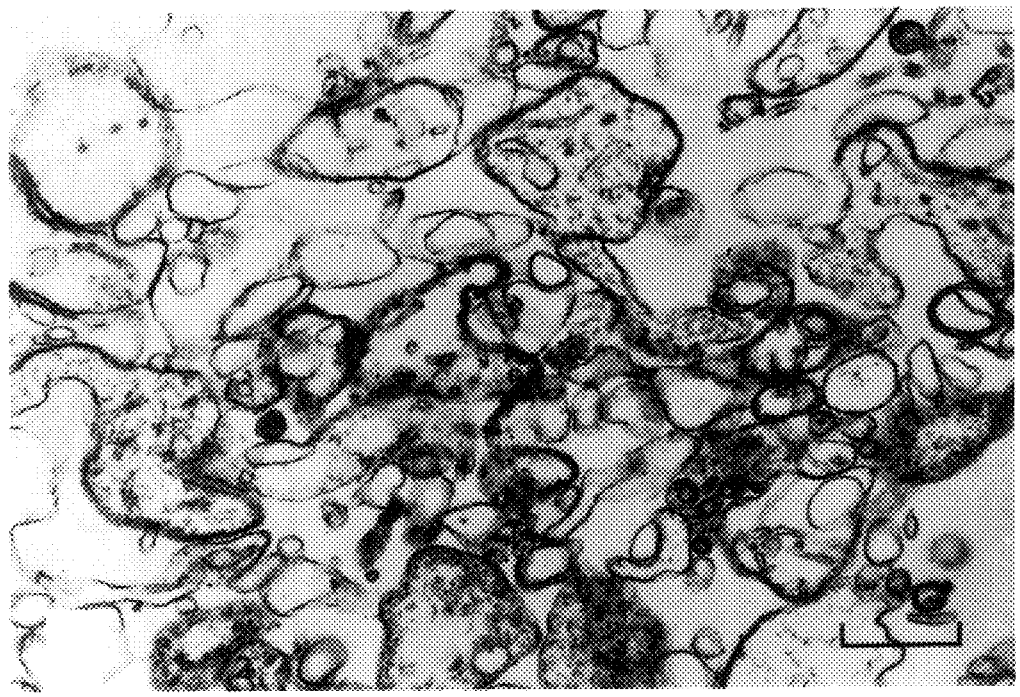
Figure 6F:
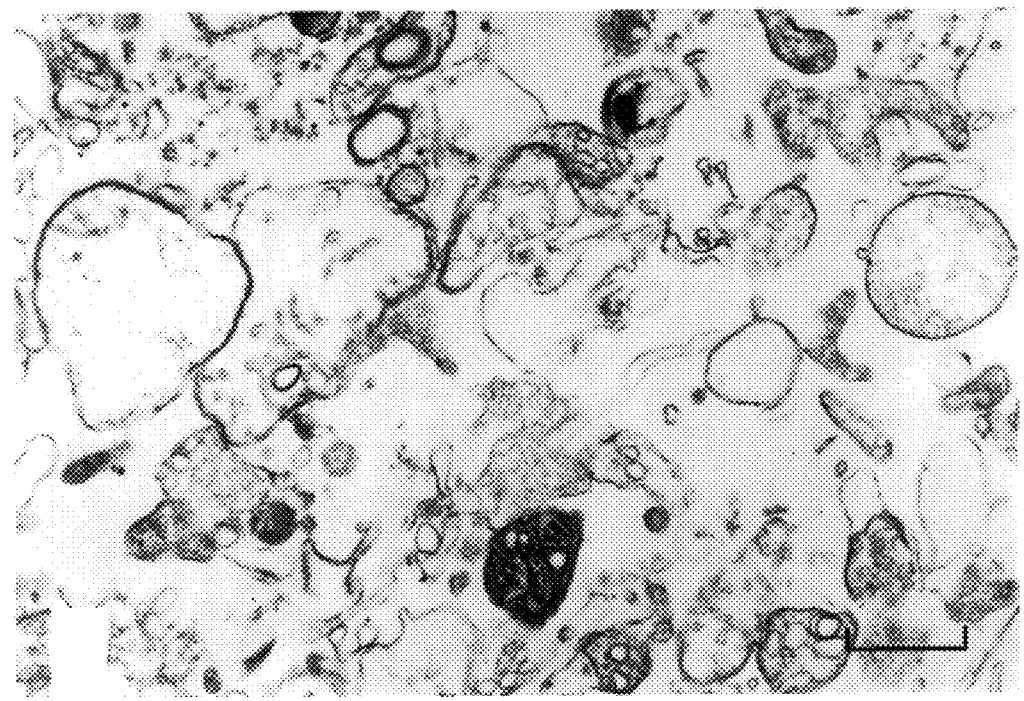

The molecule defined by anti-7A6 appears to be localized to the mitochondrial membrane Electron microscopy using immunogold labeling of digitonin permeabilized cells with anti-7A6 revealed a patchy distribution of antigens on mitochondrial organelles of Jurkat cells that had been treated by Ara-C. Immunoreactivity on frozen sections showed anti-7A6 to label mitochondria but not other organelle-associated proteins (FIG. 6A & B). Most prominent labeling of anti-7A6, however, was observed in isolated mitochondria (FIG. 6C & D). Mitochondria were isolated from normal or Ara-C induced apoptotic Jurkat cells by Percoll-metrizamide gradient centrifugation, and permeabilized by digitonin before immunogold labeling. Anti-7A6 was found to label antigens along the membrane of mitochondria that were isolated from apoptotic Jurkat cells (FIG. 6C). At a higher magnification of electron micrography, it was observed that the immunolabeling of 7A6 appeared to directly overlie on the surface of the mitochondrial inner membrane, but not within the mitochondrial matrix (FIG. 6D). In contrast, anti-7A6 showed no reactivity with mitochondria isolated from normal Jurkat cells (FIG. 6E). When an isotype-matched control antibody was used under identical conditions, no immunogold labeling was observed on mitochondria isolated from apoptotic Jurkat cells (FIG. 6F).

Anti-7A6 identifies an epitope exposed on the mitochondrial membrane protein whose expression appears to be restricted to cells undergoing apoptosis. The monoclonal antibodies and immunoreactive fragments of the invention can be used to distinguish apoptotic cells from normal cells, study the molecular mechanisms of apoptosis, diagnose samples from apoptosis-related diseases and to identify novel agonists or antagonists of apoptosis.

Reference is made to the article by Thompson, (1995, Science 267:145–1462) which describes in detail the role of apoptosis in the pathogenesis and treatment of disease. As stated in Thompson, homeostasis is maintained through a balance between cell proliferation and cell death. Physiologic cell death occurs primarily through "cell suicide" or apoptosis. Alterations in cell survival contribute to the pathogenesis of a number of human diseases, including cancer, viral infections, autoimmune diseases, neurodegenerative disorders and AIDS (acquired immunodeficiency syndrome), thus treatments designed to specifically alter the apoptotic threshold may have the potential to change the natural progression of these related diseases.

In particular, it is known that cancer is associated with the inhibition of apoptosis whereas AIDS is associated with increased apoptosis. It is within the scope of the invention that the antibody (anti-7A6) can be used in methods to detect, distinguish, monitor or quantify apoptotic cells in diagnostic applications for the treatment of both cancer and AIDS.

Further, the antibodies of the invention can be used in assays to screen for novel agents which inhibit or induce apoptosis. For example, agents which induce apoptosis in tumorgeneic cells can be identified using in vitro assays which compare the level of apoptotic cells in treated and untreated tumor samples using the anti-7A6 antibodies of the invention. Similarly, the antibodies of the invention can also be used to identify agents which inhibit the apoptosis of, for example, activated HIV-infected PBLs.

DEPOSIT

A culture of hybridoma cells which produce the anti-7A6 monoclonal antibody has been deposited as of Mar. 14, 1996 with the American Type Culture Collection (A.T.C.C.), 10801 University Boulevard, Manassas, Va. 20110–2209 U.S.A. under the terms of the Budapest Treaty and assigned A.T.C.C. No. HB-12065.

We claim:

1. A monoclonal antibody which specifically binds to an antigen on the membrane of mitochondria in apoptotic cells, said antigen
    having a molecular weight of approximately 38 kd and detectable in cells undergoing apoptosis and undetectable in normal cells.

2. The monoclonal antibody of claim 1 having mouse isotype IgG1 which is produced by the cell line on deposit with the American Type Culture Collection, A.T.C.C. No. HB 12065.

3. A hybrid cell line on deposit with the American Type Culture Collection, having A.T.C.C. Accession No. HB 12065.

4. An antibody fragment comprising a functional portion of the antigen binding domain of an antibody according to claim 1.

5. An antibody according to claim 1, which forms an immune complex with the same epitope as the monoclonal antibody produced by the hybridoma identified by ATCC Accession No. HB 12065.

6. A method of detecting and measuring cells undergoing apoptosis comprising:

(a) contacting a biological sample with a monoclonal antibody conjugated with a detector group selected from the group consisting of a fluorescent compound, a radioactive element and an enzyme; wherein said monoclonal antibody specifically binds to an antigen on the membrane of mitochondria in apoptotic cells, said antigen being detectible in cells undergoing apoptosis and undetectable in normal cells and wherein said antigen has a molecular weight of approximately 38 kd;

(b) detecting and measuring the immunological complex formed, if any, by use of a detecting and measuring means appropriate to the detector group selected; and (c) determining the amount of cells undergoing apoptosis in said biological sample as the result of the detection and measurement of the complex of step (b).

7. The method of claim 6 including the step of flow cytometic cell sorting of cells undergoing apoptosis which are bound to said conjugated monoclonal antibody.

8. A method of distinguishing between normal and apoptotic cells in a sample of human hemopoietic cell populations comprising, contacting said sample with a monoclonal antibody for a time and under conditions sufficient for formation of immunological complexes between said antibody and apoptotic cells and then detecting said immunological complexes resulting from said contact between said monoclonal antibody and cells in said sample; wherein said monoclonal antibody specifically binds to an antigen on the membrane of mitochondria in apoptotic cells, said antigen being detectible in cells undergoing apoptosis and undetectable in normal cells and wherein said antigen has a molecular weight of approximately 38 kd.

* * * * *